United States Patent
Bergmann et al.

(10) Patent No.: US 6,537,760 B1
(45) Date of Patent: Mar. 25, 2003

(54) RECEPTOR BINDING ASSAY FOR DETECTING TSH-RECEPTOR AUTO-ANTIBODIES

(75) Inventors: Andreas Bergmann, Berlin (DE); Joachim Struck, Berlin (DE)

(73) Assignee: B.R.A.H.M.S. Aktiengesellschaft, Hennigsdorf (DE)

(*) Notice: Subject to any disclaimer, the term of this patent is extended or adjusted under 35 U.S.C. 154(b) by 0 days.

(21) Appl. No.: 09/319,570

(22) PCT Filed: Dec. 3, 1997

(86) PCT No.: PCT/EP97/06767

§ 371 (c)(1),
(2), (4) Date: Aug. 4, 1999

(87) PCT Pub. No.: WO98/26294

PCT Pub. Date: Jun. 18, 1998

(30) Foreign Application Priority Data

Dec. 9, 1996 (DE) ........................................ 196 51 093

(51) Int. Cl.⁷ ...................... G01N 33/53; G01N 33/536; G01N 33/543; G01N 33/566

(52) U.S. Cl. ...................... 435/7.1; 435/7.2; 435/7.21; 435/7.93; 435/7.92; 435/7.94; 435/7.4; 435/70.1; 435/71.1; 435/71.2; 435/965; 435/65.1; 435/252.3; 435/975; 435/963; 435/320.1; 435/325; 435/73; 435/7.25; 436/501; 436/500; 436/513; 436/517; 436/518; 436/536; 436/811; 530/300; 530/350; 530/360; 530/326; 530/395; 530/854; 530/387.2

(58) Field of Search .................. 435/7.1, 7.2, 7.21, 435/7.93, 7.94, 5–6, 975, 7.92, 7.95, 7.4, 70.1, 71.1, 71.2, 965, 65.1, 252.3, 320.1, 325, 7.22, 7.23, 7.24, 7.25, 7.3, 7.31–7.36, 7.8, 963; 436/501, 518, 500, 517, 811, 506, 536, 513, 508; 530/326, 395, 854, 387.3, 387.2, 350, 300, 360

(56) References Cited

U.S. PATENT DOCUMENTS

| | | | | |
|---|---|---|---|---|
| 5,354,654 A | * | 10/1994 | Ligler et al. ................... | 435/5 |
| 5,501,955 A | | 3/1996 | Bergmann | |
| 5,814,461 A | * | 9/1998 | Bergmann et al. ........... | 435/7.1 |
| 5,837,460 A | * | 11/1998 | Von Feldt et al. .............. | 435/6 |
| 5,886,148 A | * | 3/1999 | Sergre et al. ................ | 530/350 |
| 5,998,153 A | * | 12/1999 | Baker et al. ................ | 435/7.21 |

FOREIGN PATENT DOCUMENTS

| | | | | |
|---|---|---|---|---|
| DE | 4237430 | * | 3/1994 | ........... C07K/15/06 |
| DE | 4328070 | * | 11/1994 | .......... G01N/33/53 |
| DE | WO 95/06258 | * | 3/1995 | .......... G01N/33/74 |
| DE | 19522171 | | 8/1996 | |
| DE | WO 98/26294 | * | 12/1996 | .......... G01N/33/76 |
| EP | 0719858 A2 | | 7/1996 | |

OTHER PUBLICATIONS

Kronus, TSH receptor antibody (TRAb) kit., 1993.*
IBL Thyrotropin Receptor Autoantibodies, 1993.*
Bruin et al., "Anti Thyrotropin Receptor antibodies in graves Disease as Demonstracted by Immuno Precipitation Assay", Acta Endocrinologica, vol. 102, No. 1, 1983, pp. 49–56.*
Yavin et al., "Monoclonal antibodies to the Thryrotropin receptor Implications for Receptor Structure and the Action of Autoantibodies in Graves Disease", Proc. Natl. Acad. sci., USA vol. 78, No. 5, 1981, pp. 3180–3184.*
Cho et al., Evaluation of serum basal thyrotropin levels and thyropin receptor antibody activities as prognostic markers for discontinuation of antithyroid drug–treatment in patients with Graves–disease., Clinical Endocinology, 1992, vol. 36, No. 6, June,p.*
Tandon et al., T cell responses to synthetic TSH receptor peptides in Graves' disease., Clin. Exp. Immunol., 1992, vol. 89, No. 3, pp. 468–473.*
Maggio, "Enzyme–Immunoassay", Immunoenzyme technique, pp. 186–187, copyright 1980 by CRC Press, Inc.*
Loeffler et al., "Compositions of Different Assays for the Thyroid–Stimulating Antibody of Graves' Disease", Journal of Clinical Endocrinology and Metabolism, vol. 57, No. 3, S. 603–608, 1983.
J.R. Baker et al., "Partial Characterization and Clinical Correlation of Circulating Human Immunoglobulins Directed against Thyrotropin Binding Sites in Guinea Pig Fat Cell Membranes", Journal of Clinical Investigation, vol. 72, S. 1487–1497 (1983).
D.O. Morgan et al., "Plate Binding Assay for Monoclonal Anti–Receptor Antibodies", Endocrinology, vol. 116, No. 3, S. 1224–1226, (1985).
E.A. Pierce et al., "A Radiometric Immunosorbent Assay for the Detection of Anti–hormone–Binding Protein Antibodies", Analytical Biochemistry 153, S.67–74 (1986).
D.S.Dwyer et al., "An Enzyme–Linked Immunoabsorbent Assay for Measuring Antibodies against Muscle Acetylcholine Receptor", Journal of Immunological Methods, 57 (1983), S. 111–119.

(List continued on next page.)

Primary Examiner—Christopher L. Chin
Assistant Examiner—Lisa V. Cook
(74) Attorney, Agent, or Firm—Pillsbury Winthrop LLP

(57) ABSTRACT

In a competitive receptor binding assay for detecting TSH-receptor auto-antibodies in a biological sample, the sample is reacted in a reaction mixture which contains (i) a TSH-receptor or TSH-receptor preparation; (ii) a primary competitor, for example labelled TSH; and (iii) an agent for separating a complex composed of the TSH-receptor and the elements bound thereto of the reaction mixture from the liquid phase. According to the invention, the reaction is carried out in the presence of at least one monoclonal or polyclonal antibody specific against a partial peptide sequence of the TSH eceptor. This specific antibody is used to immobilize a complex of TSH-receptor and primary competitor and/or as secondary competitor for another part of the TSH-receptor auto-antibodies expected in a sample. The primary or secondary competitors are or can be selectively labelled.

19 Claims, 2 Drawing Sheets

OTHER PUBLICATIONS

Figure 1:
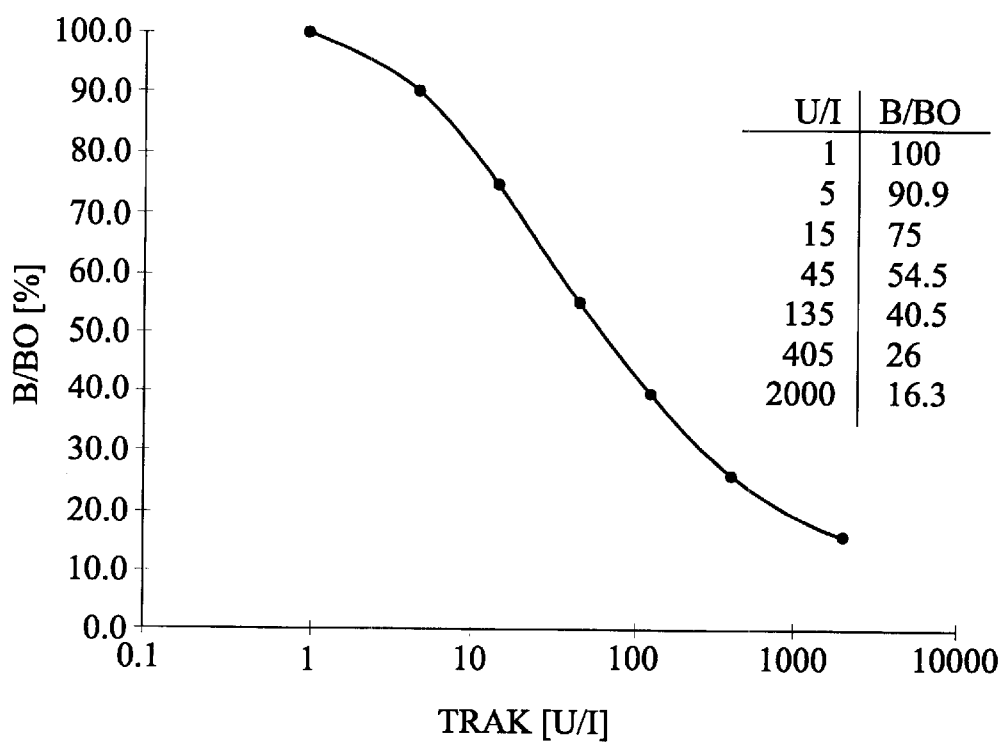

Costagliola et al., "Binding Assay for Thyrotropin Receptor Autoantibodies Using the Recombinant Receptor Protein", J. Clin. Endocrinology and Metabolism, (1992), vol. 75(6); S. 1540–1544.

M.Z. Atassi et al., "Localization and synthesis of the hormone–binding regions of the human thyrotropin receptor" (1991), Proc., Nat'l. Sci. USA, vol. 88, pp. 3613–3617.

S. Sakata et al., "Biological activities of rabbit antibodies against synthetic human thyrotropin receptor peptides representing throtropin binding regions", (1992) Biochemical and Biophysical Communications vol. 182, No. 3, pp. 1369–1375.

S. Costagliola et al., "Second Generation Assay for Thyrotropin Receptor Antibodies Has Superior Diagnostic Sensitivity for Graves' Disease", Journal of Clinical Endocrinology and Metabolism, vol. 84, No. 3, S. 90–97, 1999 (published after the relevant priority and application dates).

Libert et al., Cloning, Sequencing and Expression of the Human Thyrotropin . . . , Biochem. Biophys. Res. Commun., 1989, 165:1250–1255.

Nagayama et al., Molecular Cloning, Sequence and Functional Expression . . . , Biochem. Biophys. Res. Commun., 1989, 165:1184–1190.

Naagayama et al., The Thyrotropin Receptor 25 Years . . . , Molecular Endocrinology, 1992, vol. 6, No. 2, pp. 145–156.

Morgenthaler et al., In vitro synthesized TSH . . . , Exp. Clin. Endocrinol Diabetes 104, 1996, Suppl. 4, pp. 56–59.

Seetharamaiah et al., A Recombinant Extracellular Domain . . . , Endocrinology, 1994, vol. 134, No. 2, pp. 549–554.

Dallas et al., Thyrotropin (TSH) Interacts with Multiple Discrete . . . , Endocrinology, 1994, vol. 134, No. 3, pp. 1437–1445.

Johnstone et al., Monoclonal antibodies that recognize the native human . . . , Mol. Cell. Endocrinol. 105, 1994, pp. R1–R9.

Seetharamaiah et al., Generation and Characterization of Monoclonal . . . , Endocrinology, 1995, vol. 136, No. 7, pp. 2817–2824.

Nicholson et al., Monoclonal antibodies to the human TSH . . . , J. Mol. Endocrinol., 1996, 16, pp. 159–170.

Ropars et al., One Monoclonal Antibody to Human Thyrotropin . . . , Cell. Immunol., 1995, 161, pp. 262–269.

Ludgate et al., Use of the recombinant human thyrotropin . . . , Mol. Cell. Endocrinol. 73, 1990, pp. R13–R18.

Furmaniak et a., The Structure of Thyroid Autoantigens, Autoimmunity, 1990, vol. 7, pp. 63–80.

Ohmori et al., Development of Chicken Antibodies Toward the Human . . . , Biochem. Biophys. Res. Commun., 1991, vol. 174, No. 1, pp. 399–403.

Endo et al., Rabbit Antibodies Toward Extracellular Loops . . . , Biochem. Biophys. Res. Commun., 1991, vol. 181, No. 3, pp. 1035–1041.

Filetti et al., Recombinant Human Thyrotropin (TSH) Receptor . . . , J. Clin. Endocrinol. Metab., 1991, vol. 72, No. 5, pp. 1096–1101.

Costagliola et al., Monoclonal Antiidiotypic Antibodies Interact . . . , Endocrinology, 1991, vol. 128, No. 3, pp. 1555–1561.

Gupta, Thyrotropin Receptor Antibodies: Advances and Importance . . . , Clin. Biochem., 1992, vol. 25, pp. 193–199.

Marion et al., Characterization of Monoclonal Antibodies . . . , Enocrinology, 1992, vol. 130, No. 2, pp. 967–975.

Sanders et al., Production and Characterisation of TSH . . . , J. Endocrinol. Invest. 19, 1996, Suppl. To No. 6, pp. 33.

Derwahl et al., Measurement of Stimulating TSH Receptor . . . , Exp. Clin. Endocrinol. 100, 1992, pp. 75–79.

Ohmori et al., Immunization with human thyrotrophin . . . , J. Endocrinol., 1992, 135, pp. 479–484.

Hirooka et al., Generation of bioactive rabbit antibodies . . . , Med. Sci. Res., 1992, 20, pp. 639640.

Leedman et al., Human Thyrotropin Receptor Subunits . . . , J. Clin. Endocrinol. Metab., 1989, vol. 69, No. 1, pp. 134–141.

Desai et al., Dual Mechanism of Perturbation of Tyrotropin–Mediated . . . , J. Clin. Endocrinol. Metab., 1993, vol. 77, No. 3, pp. 658–663.

Matsuba et al., Expression of Recombinant Human Thyrotropin . . . , J. Biochem. 118, 1995, pp. 265–270.

Bruin et al: "Anti Thyrotropin Receptor Antibodies in Graves Disease as Demonstrated Directly by Immuno Precipitation Assay", Acta Endocrinol 102 (1). 1983. 49–56 Coden: ACENA7 ISSN: 0001–5598, XP002061960.

Yavin et al: "Mono Clonal Antibodies to the Thyrotropin Receptor Implications for Receptor Structure and the Action of Auto Autobodies in Graves Disease", Proc Natl Acad Sci U S A 78 (5). 1981. 3180–3184. Coden; PNASA6 ISSN: 0027–8424 XP002061961.

* cited by examiner

SEQUENCE LISTING

<160> NUMBER OF SEQ ID NOS: 5

<210> SEQ ID NO 1
<211> LENGTH: 20
<212> TYPE: PRT
<213> ORGANISM: Homo sapiens

<400> SEQUENCE: 1

Gly Gly Met Gly Cys Ser Ser Pro Pro Cys Glu Cys His Gln Glu Glu
 1               5                   10                  15

Asp Phe Arg Val
            20

```
<210> SEQ ID NO 2
<211> LENGTH: 23
<212> TYPE: PRT
<213> ORGANISM: Homo sapiens

<400> SEQUENCE: 2

His Gln Glu Glu Asp Phe Arg Val Thr Cys Lys Asp Ile Gln Arg Ile
 1               5                  10                  15

Pro Ser Leu Pro Pro Ser Thr
            20

<210> SEQ ID NO 3
<211> LENGTH: 15
<212> TYPE: PRT
<213> ORGANISM: Homo sapiens

<400> SEQUENCE: 3

Lys Asn Gln Lys Lys Ile Arg Gly Ile Leu Glu Ser Leu Met Cys
 1               5                  10                  15

<210> SEQ ID NO 4
<211> LENGTH: 21
<212> TYPE: PRT
<213> ORGANISM: Homo sapiens

<400> SEQUENCE: 4

Asp Glu Ile Ile Gly Phe Gly Gln Glu Leu Lys Asn Pro Gln Glu Glu
 1               5                  10                  15

Thr Leu Gln Ala Phe
            20

<210> SEQ ID NO 5
<211> LENGTH: 20
<212> TYPE: PRT
<213> ORGANISM: Homo sapiens

<400> SEQUENCE: 5

Tyr Glu Leu Ile Glu Asn Ser His Leu Thr Pro Lys Lys Gln Gly Gln
 1               5                  10                  15

Ile Ser Glu Glu
            20
```

RECEPTOR BINDING ASSAY FOR DETECTING TSH-RECEPTOR AUTO-ANTIBODIES

This application is the national phase of international application PCT/EP97/06767 filed Dec. 3, 1997 which designated the U.S. and claims priority to application number 19651093.7, filed Dec. 9, 1996 in Germany.

The present invention relates to a competitive receptor binding assay for the determination of TSH receptor autoantibodies which occur in autoimmune diseases of the thyroid, in particular in Graves' disease.

It is known that many diseases in which the thyroid is involved are autoimmune diseases in which autoantibodies against molecular structures of the thyroid are formed and, in conjunction with the disease, begin to act as autoantigens. The most important known autoantigens of the thyroid are thyroglobulin (Tg), thyroid peroxidase (TPO) and in particular the TSH receptor (TSHr) (cf. Furmaniak J. et al., Autoimmunity 1990, Vol. 7, pages 63–80).

The TSH receptor is a receptor which is localized in the thyroid membrane and to which the hormone TSH (thyroid-stimulating hormone or thyrotropin) secreted by the pituitary gland binds and thus triggers the secretion of the actual thyroid hormone, in particular thyroxine. The TSH receptor belongs to the receptor family, comprising the G-protein-coupled glycoprotein receptors having a large amino terminal extracellular domain, to which the LH/CG and the FSH receptor also belong. The chemical structure of the TSH receptor, i.e. the sequence of the DNA coding for it and the amino acid sequence, derivable therefrom, of the receptor itself, was elucidated at the end of 1989 (cf. Libert F. et al., Biochem. Biophys. Res. Commun. 165: 1250–1255; Nagayama Y. et al., Biochem. Biophys. Res. Commun. 165: 1184–1190; cf. also EP-A-0433509 and WO-A-91/09121; and WO-A-91/09137; WO-A-91/10735 and WO-A-91/03483; furthermore, Yuji Nagayama & Basil Rapoport in: Molecular Endocrinology, Vol. 6 No. 2, pages 145–156, and the literature cited therein).

It is generally known that stimulating autoantibodies play a role in the thyroid autoimmune disease known as Graves' disease, said autoantibodies being formed against the TSH receptor and interacting with it so that the thyroid is stimulated, which manifests itself as hyperthyroidism. The determination of autoantibodies against the TSH receptor is thus of considerable clinical importance for the diagnosis of Graves' disease.

Apart from assay methods in which experimental animals or special cell cultures play a role and which are now in particular of historical interest (cf. Schumm-Draeger et al., Akt. Endokr. Stoffw. 10 (1989), pages 90–102), it has been possible to date to determine TSH receptor autoantibodies essentially according to two basic methods (cf. Morgenthaler N. G. et al., Exp Clin Endocrinol Diabetes 104 (1996) Suppl 4, pages 56–59): In cell stimulation tests, the presence of stimulating TSH receptor autoantibodies, which are frequently referred to in the literature with the abbreviation TSI (TSI=thyroid stimulating immunoglobulins), manifests itself by the fact that specific functions of suitable cells which have natural or recombinant TSH receptors in their cell membrane and come into contact with a sample containing autoantibodies are triggered or enhanced by stimulation, in particular the formation of cAMP (cyclic adenosine monophosphate). In these tests also referred to as bioassays, the stimulating effect is selectively measured, but the measurement is extremely complicated and therefore not very suitable for routine clinical diagnostics.

Alternatively, autoantibodies can also be determined using competitive receptor binding assays, in particular radio receptor assays, for example with the use of the TRAK-Assay® from B.R.A.H.M.S Diagnostica GmbH. For the determination of TSH receptor autoantibodies by this conventional method, the autoantibodies to be determined and originating from a serum sample are allowed to compete in the liquid phase with a radiolabelled bovine TSH competitor for the binding sites of a detergent-solubilized porcine TSH receptor (cf. Southgate, K. et al., Clin. Endocrinol. (Oxford) 20, 539–541 (1984); Matsuba T. et al., J. Biochem. 118, pages 265–270 (1995); EP 719 858 A2; product information on the TRAK-Assay® from B.R.A.H.M.S Diagnostica GmbH). To determine the labelled TSH bound to the receptor preparation, after incubation is complete the TSH receptor is separated from the liquid phase using a precipitation reagent and a subsequent centrifuging step. The receptor-bound labelled TSH is determined by measuring the radioactivity bound in the sediment. Since the determination is based on competition between labelled TSH and the autoantibodies to be determined for common binding sites of the TSH receptor, all those autoantibodies, and only those antibodies, which actually compete with TSH are determined in this method. Such competing autoantibodies capable of inhibiting the TSH binding are also referred to in the literature as TBII (TBII=thyrbtropin-binding inhibitory immunoglobulin), and the extent of their activity is also stated as a percentage so-called TBII activity.

It has long been known that heterogeneous autoantibody populations of different compositions are formed in autoimmune diseases of the thyroid. The stimulating autoantibodies and the autoantibodies competing with TSH are only partly identical, i.e. there are stimulating autoantibodies which do not compete with TSH and there are also autoantibodies competing with TSH which do not have a stimulating effect. In addition, autoantibodies which neither have a stimulating effect nor compete with TSH may also be present (cf. for example Ludgate M. et al., Mol. Cell. Endocrinol. 73 (1990), R13–R18; Filetti S. et al., J. Clin. Endocrinol. Metab. 72, pages 1096–1101, 1991; Morgenthaler N. G. et al., Exp Clin Endocrinol Diabetes 104 (1996) Suppl 4, pages 56–59, and literature cited therein). As a consequence of this, autoantibodies are detectable with the aid of radio receptor assays only in about 80% to 90% of patients suffering from Graves' disease (cf. for example Rationelle Diagnostik in der Endokrinologie [Rational Diagnostics in Endocrinology], Thieme Verlag, page 49, paragraph: TSH Rezeptorautoantikörper (TSH-RAK) [TSH receptor autoantibodies (TSH-RAB)]; or Ropars A. et al., Cell. Immunol. 161, pages 262–269 (1995); Ohmori M. et al., Biochem. Biophys. Res. Commun. 174, No. 1 (1991), pages 399–403; Endo T. et al., Biochem. Biophys. Res. Commun. 181, No. 3 (1991), pages 1035–1041; Gupta M. K., Clin. Biochem. 25, pages 193–199 (1992)). Since the failure to detect a part of the autoantibodies occurring in Graves' disease is due to the measuring principle of the competitive radio receptor assays to date, it has already been proposed, in spite of considerable complexity, to carry out a supplementary bioassay measurement for determining stimulating TSI autoantibodies if a discrepancy between the clinical picture of a patient suffering from Graves' disease and the result of the determination of competing TBII autoantibodies is evident (Derwahl M. et al., Exp. Clin. Endocrinol. 100 (1992), pages 75–79).

Apart from the limited clinical value described, the competitive radio receptor assays known to date for the detection of TSH receptor autoantibodies have fundamental disadvantages of a practical nature which are due to the fact that the binding capability of TSH receptor preparations is generally very sensitive to changes in the receptor or in the biomolecule bound by it. The binding of biomolecules of a peptide or protein nature, for example of hormones or autoantibodies, to receptors is as a rule very complex, and the formation of a specific bond between receptor and biomolecule is very much more sensitive to structural changes, in particular in the receptor, than is the case with a conventional antigen/antibody binding pair, which is the basis of most immunoassays in which the receptors play no role. Attempts to immobilize and/or to label the TSH receptor led as a rule to structural changes which greatly impaired the functionality of the receptor. As a consequence of this, many basic assay types which are available in immunoassays utilizing an antibody/antigen bond, in particular those in which immobilized binding partners are used and, at the end of the measurement, the concentration of a tracer bound to a solid phase is determined directly, or in which bulky molecules, such as enzymes, enzyme substrates or chemiluminescent tracers, are used for labelling, could not be used to date in practice for carrying out receptor binding assays for the determination of TSH receptor autobodies. Since the measurement of a tracer bound to a solid phase forms the basis of most automatic assay units for series measurements, it has not been possible to date to carry out the known assays for the determination of TSH receptor autoantibodies on such automatic units.

The patent DE 43 28 070 C1 describes a type of receptor binding assay which operates according to the coated tube technique, in which the difficulty of preparing labelled or immobilized functional receptor preparations is overcome by binding to the solid phase components of a competing reaction system which, so to speak, represents a "shadow" of the actual receptor binding reaction. However, the disclosed principle of the method has proved too complicated and therefore not very feasible for providing assays for routine clinical diagnostics. The general statements in said patent on the problems of receptor binding assays in general and of those for the determination of TSH receptor autoantibodies in particular are hereby expressly incorporated by reference.

EP-B-0 488 170 furthermore discloses cell-free receptor binding tests in which recombinant fusion receptors comprising an amino terminal receptor protein and a carrier protein, in particular the constant fragment (Fc) of the heavy chain of an immunoglobulin, are used, which fusion receptors are coupled to a solid phase by means of an antiserum or of a monoclonal antibody. The receptors discussed do not belong to the class consisting of the high molecular weight G-protein-coupled glycoprotein receptors. Furthermore, immobilization by binding a carrier protein which is the Fc fragment of an immunoglobulin is not very suitable for receptor binding assays with the aid of which autoantibodies are to be determined, since the autoantibodies themselves belong to the immunoglobulins and can bind to the immobilization system.

DE 41 20 412 C1 furthermore discloses a method for the determination of autoantibodies, in which the disturbance of a sandwich which is composed of an immobilized specific autoantibody, a crude autoantigen in the form of a suitable organ extract, in particular TPO, and a labelled further antibody by autoantibodies against the autoantigen which are present in the sample is used for the determination. In terms of disturbance, autoantibodies present in a sample can in principle interact with each individual immunological bond or with both immunological bonds which is or are involved in the structure of the complete sandwich. Owing to the described sensitivity of the receptors and the lack of autoantibodies having the required selectivity, it has not been possible to date to apply this principle to cases where the autoantigen is a receptor and the labelled binding partner is a labelled hormone, such as, for example, TSH.

After the molecular structure of the TSH receptor had been elucidated, monoclonal and polyclonal autoantibodies against human recombinant TSH receptors, against the N-terminal extracellular fragment (comprising 398 amino acids without the signal peptide) of such receptors and against conjugates of shorter receptor peptide partial sequences were prepared by numerous working groups with the aim of elucidating the epitopes of the TSH receptor which are responsible for TSH binding and the antibody binding (cf. for example N. G. Morgenthaler et al., Exp Clin Endocrinol Diabetes 104 (1996) Suppl 4, pages 56–59; Seetharamaiah G. S. et al., Endocrinology 134, No. 2, pages 549–554 (1994); Desai R. K. et al., J. Clin. Endocrinol. Metab. 77:658–663, 1993; Dallas J. S. et al., Endocrinology 134, No. 3, pages 1437–1445 (1994); Johnstone A. P. et al., Mol. Cell. Endocrinol. 105 (1994), R1–R9; Seetharamaiah G. S. et al., Endocrinology 136, No. 7, pages 2817–2824 (1995); Nicholson L. B. et al., J. Mol. Endocrinol. (1996) 16, pages 159–170; Ropars A. et al., Cell. Immunol. 161, pages 262–269 (1995); Ohmori M. et al., Biochem. Biophys. Res. Commun. 174, No. 1 (1991), pages 399–403; Endo T. et al., Biochem. Biophys. Res. Commun. 181, No. 3 (1991), pages 1035–1041; Costagliola S. et al., Endocrinology 128, No. 3, pages 1555–1562, 1991; Marion S. et al., Endocrinology 130, No. 2, pages 967–975 (1992); J. Sanders et al., J. Endocrinol. Invest. 19 (Suppl. No. 6), 1996, and further publications cited in the stated publications). The various antibodies were tested for their binding behaviour with respect to the TSH receptor or partial sequences thereof produced recombinantly and in particular with regard to their ability to disturb the binding of TSH to various forms or fragments of the TSH receptor. Since the various polyclonal or monoclonal antibodies had been produced by immunizing different animals and/or using recombinant material from different expression systems and moreover recombinantly produced TSH receptors of different origin or peptide fragments thereof are frequently used in the binding tests, and since furthermore it was found that the glycosylation and/or correct folding of the receptor peptide was likely to be decisive for the binding of many antibodies, the epitope structure of natural TSH receptors and the epitope-specific binding behaviour of the autoantibodies occurring in polyclonal autoantibody populations has not yet been fully explained.

In the publication by Dallas J. S. et al., Endocrinology 134, No. 3, pages 1437–1445 (1994), for example, a partial recombinant TSH receptor produced with the aid of the baculovirus/insect cell expression system and having the amino acids of the extracellular domain of the human TSH receptor without the N-terminal signal peptide is used to immunize rabbits, and specific antibody fractions are obtained from the resulting immunoglobulin fractions by affinity chromatography using synthetic peptides each having about 20 amino acids. Said specific antibody fractions are then investigated with respect, inter alia, to their suitability for blocking the binding of TSH to a solubilized porcine TSH receptor in a commercial receptor binding assay. The antibodies showed no stimulatory activity.

The publication by Seetharamaiah G. S. et al., Endocrinology 136, No. 7, pages 2817–2824 (1995) describes how the same partial recombinant TSH receptor as that in the above publication was used for immunizing mice and for preparing monoclonal antibodies against individual epitopes of the TSH receptor according to standard techniques. A similar procedure is described in Nicholson L. B. et al., J. Mol. Endocrinol. (1996) 16, pages 159–170.

According to Seetharamaiah G. S. et al., Endocrinology 134, No. 2, pages 549–554 (1994), a partial recombinant TSH receptor prepared as above is subsequently folded and tested with respect to its suitability for binding radiolabelled TSH. For this purpose, it is reacted with radiolabelled TSH in the liquid phase. To separate the resulting complex as quantitatively as possible from the reaction mixture, an antibody which was produced by immunizing rabbits with a conjugate of a peptide fragment which contains the amino acids 357 to 372 of the complete TSH receptor sequence and which had been shown not to inhibit the binding of TSH to the unfolded partial recombinant TSH receptor is then added as part of a precipitation system (Desai R. K. et al., J. Clin. Endocrinol. Metab. 77:658–663, 1993). The added antibody or the complexes containing it and bound radiolabelled TSH is or are then precipitated with the aid of protein A, which binds unspecifically to any antibodies. Under the test conditions, the binding of protein A to the receptor-bound antibody does not appear to impair the simultaneous TSH binding.

The knowledge obtained using antibodies against recombinant TSH receptors or parts thereof led to the proposal to determine TSH receptor autoantibodies by using a third principle known per se, in the form of an immunoprecipitation assay, in which a preparation of an extracellular part of a recombinant TSH receptor labelled by incorporating $^{35}$S-labelled methionine is used as a reagent for the precipitation. Such an assay has the selectivity neither for TSI nor for TBII. (N. G. Morgenthaler et al., Exp Clin Endocrinol Diabetes 104 (1996) Suppl 4, pages 56–59). However, the preparation of the labelled receptor by in vitro translation is extremely complicated and expensive, and there are no measuring apparatuses which are suitable for routine clinical measurement of the radiation emitted by $^{35}$S. The method is therefore not suitable as a method of measurement for routine clinical diagnostics.

It is the object of the present invention to provide a competitive receptor binding assay for the determination of TSH receptor autoantibodies which does not have the described disadvantages of such competitive receptor binding assays of the prior art.

In particular, it is the object of the present invention to provide an improved competitive receptor binding assay for the determination of TSH receptor autoantibodies, in which it is possible to immobilize the TSH receptor complexes formed from the reactants of the assay method for the measurement on a conventional solid phase and to overcome the existing restrictions with regard to suitable tracers, so that an automatic procedure for such receptor binding assays is also possible.

In particular, it is furthermore the object of the present invention to design such improved competitive receptor binding assays for the detection of TSH receptor autoantibodies in such a way that greater clinical value is obtained compared with such assays of the prior art.

It is furthermore the object of the present invention to provide reagent kits for carrying out such improved receptor binding assays in routine clinical diagnostics.

Said objects are achieved in a competitive receptor binding assay according to the precharacterizing clause of claim 1 at least partly by radio receptor assays which have the features described [lacuna] the characterizing clause of claim 1.

Advantageous embodiments of the improved receptor binding assays according to the invention are described in the subclaims, in particular in conjunction with the following explanations in the present description.

The object of providing a corresponding reagent kit is achieved by a reagent kit for carrying out a method according to the invention which in each case contains at least one of the components (i), (ii) and (iii) according to claim 15.

In order to cover various possible embodiments for the receptor binding assay of the present invention, a general mode of expression, which will be explained below by way of introduction, is used in claim 1 both for describing known features of such receptor binding assays and for characterizing those features in which a receptor binding assay according to the invention differs from one of the prior art:

As explained in the introductory part, the known competitive receptor binding assays, all of which are designed as radio receptor assays, contain the following assay components:

A solubilized TSH receptor (i), in particular a solubilized natural animal (porcine) TSH receptor obtained from animal thyroid membranes.

Furthermore, the known radio receptor assays contain radiolabelled bovine TSH (ii) which competes with TSH receptor autoantibodies from a serum sample (TBII) for common binding sites on the TSH receptor used. Since this competition is that which has been of primary importance to date and also permits determination of the predominant proportion of autoantibodies occurring, namely 80 to 90%, the labelled TSH of the prior art is covered by the definition "primary competitor" used in claim 1. However, this definition also includes other forms of "primary competitors", the use of which was permitted for the first time by the present invention. Thus, labelled selective antibodies against the TSH receptor, as described in more detail below, can also be used as competitors for TBII or optionally other autoantibody fractions. Furthermore, owing to the competition with TBII, a TSH bound to a solid phase should also be capable of fulfilling the definition "primary competitor".

As also explained at the outset, in the prior art complexes of the TSH receptor and components of reaction mixture which are bound thereto, i.e. labelled TSH and autoantibodies, are precipitated from the reaction mixture by means of a precipitation reagent and are separated from said reaction mixture by centrifuging. In the meaning of the precharacterizing clause of claim 1, the precipitation reagent is to be regarded as an agent according to (iii). In the case of a competitive receptor binding assay according to the invention, such an agent (iii) corresponds to a reactant which is bound to a solid phase and is primarily a specific TSH receptor antibody which is immobilized on a solid phase but, according to a "mirror-image" embodiment, can also be a TSH bound to a solid phase.

A discovery essential for the present invention is that it is possible:is possible [sic] immobilization of a natural TSH receptor too (i.e. of human, animal or recombinant TSH receptor whose folding/glycosylation corresponds at least essentially to a naturally occurring TSH receptor) from solubilized TSH receptor preparations of any kind with the aid of immobilized selective antibodies which are directed specifically against a suitable partial sequence of the TSH receptor, without the binding capability of the TSH receptor with respect to TBII autoantibodies and labelled TSH being significantly impaired. This discovery therefore created the precondition for carrying out a receptor binding assay for the determination of TSH receptor autoantibodies in such a way that the amount of the bound labelled competitor, for example of the primary competitor radiolabelled TSH, in the form bound to a solid phase can be determined. Surprisingly, however, it was furthermore found that, by immobilizing the TSH receptor on a solid phase with the aid of selective TSH receptor antibodies, it is possible considerably to improve the clinical value of competitive receptor binding assays for the determination of TSH receptor autoantibodies. As explained in more detail below, it was in fact found that, with a suitable choice of the specific antibody bound to the solid phase, the assay system contains at least one further binding site for which autoantibodies from the sample can compete.

If the antibody bound to a solid phase is chosen so that it acts as a "secondary competitor" which competes with autoantibodies of the sample other than the TBII determined by competition by. the "primary competitor", an increase in the clinical value is achieved. In fact, the resulting measuring system is one which can be regarded as analogous to the assay system schematically shown in FIG. 3 in DE 41 20 412, in which system there is a double disturbance at different binding sites of a sandwich by heterogeneous polyclonal autoantibodies from a patient's sample. Since such a disturbance is sufficient to prevent binding of the tracer to the solid phase, the measuring range is extended and the sensitivity increased. Said variant using two antibodies and a crude antigen is also described by U.S. Pat. No. 5,501,955.

It has now surprisingly been found that, in the method according to the invention, with the use of, for example, a specific antibody which had been produced against a synthetic peptide having the amino acids 20 to 39 of the amino acid sequence of the complete TSH receptor (including signal peptide), all patients classed as Graves' disease patients on the basis of clinical symptoms were determined as autoantibody-positive, although only 80% had been determined as positive by the conventional radio receptor assay. By using a "secondary competitor" which competes with autoantibodies other than TBII which occur during Graves' disease, it is possible considerably to improve the clinical value of the receptor binding assay for the diagnosis of Graves' disease.

The "secondary competitor" preferably competes with autoantibodies (TSI autoantibodies) which are determined to be stimulating in the cell stimulation test and, owing to lack of competition with TSH, are not detected by the conventional radio receptor assay. However, it is not necessary for the autoantibodies with which the "secondary competitor" competes actually to have a stimulating effect and hence to enhance the clinical symptoms of Graves' disease. The autoantibodies with which the "secondary competitor" is in competition may also belong to an autoantibody subpopulation which has a blocking effect or is unimportant for the actual pathological process. As long as such an autoantibody subpopulation occurs always or frequently in the serum of patients suffering from Graves' disease, the clinical value of the receptor binding assay will be greater than that of the conventional radio receptor assay which detects only TBII autoantibodies.

Suitable selective antibodies which form preferred "secondary competitors" are therefore in particular those which are directed against fragments of the TSH receptor which do not participate in the TSH binding but against which autoantibodies are formed in Graves' disease. The investigations to date using polyclonal antibodies purified by affinity chromatography or antibodies prepared as monoclonal antibodies resulted in some fragments of the TSH receptor being particularly suitable binding regions for selective antibodies. In the interpretation of the literature data to date, however, it should be noted that most selective antibodies were produced against recombinantly produced TSH receptor peptides or synthetic peptide fragments and are therefore probably of sequential nature. A major part of the antibodies described in nature furthermore proved to be ineffective in the cell stimulation test. This indicates that, in spite of competition with autoantibodies from sera, it is not possible to equate the synthetically produced antibodies with the autoantibodies to be determined. Furthermore, owing to the folding of the natural TSH receptor and its glycosylation, the binding behaviour of the synthetically produced antibodies on native TSH receptor preparations may differ from the binding behaviour of synthetic peptides or recombinantly produced TSH receptor fragments. With the knowledge of the teaching of the present invention, however, it is possible in specific cases, in relatively simple routine tests, to determine the suitability of special specific antibodies for the method according to the invention and their ability to act as a "secondary competitor".

The tests described below were carried out with the use of an immobilized specific antibody which is known to bind to a peptide from the range of the amino acids 20 to 39 of the complete TSH receptor, and of labelled bovine TSH as the conventional tracer ("primary competitor"). The antibody used was a monoclonal antibody which had been selected and prepared after immunization with the aid of a conjugate from the corresponding synthetic peptide by the customary hybridoma technique. The literature has described various polyclonal or monoclonal specific antibodies which likewise bind to the same region or overlapping regions of the amino terminal end of the extracellular domain of the TSH receptor (cf. Dallas J. S. et al., Endocrinology 134, No. 3, pages 1437–1445 (1994); Seetharamaiah G. S. et al., Endocrinology 136, No. 7, pages 2817–2824 (1995); Nicholson L. B. et al., J. Mol. Endocrinol. (1996) 16, pages 259–270; Ohmori M. et al., J. Endocrinol. (1992) 135, pages 479–484; Endo T. et al., Biochem. Biophys. Res. Commun. 177, pages 145–150 (1991); Hirooka Y. et al., Med. Sci. Res. 1992, 20, pages 639–640). The preparation techniques and antibody types described in said publications are in principle suitable for replacing the antibody used specifically in the tests, but it should be noted that it is known that antibodies against closely neighbouring sequences of the TSH receptor may belong to very different antibody types.

As an alternative to the antibody which is used in the Examples and is directed against the amino acids 20 to 39 of the human TSH receptor, antibodies which were produced, for example, against the regions 287 to 301, 361 to 380 or 739 to 758 are also suitable. The special properties should however be checked in specific cases on the basis of the tests described below.

If the original assay design of the conventional radio receptor assay is departed from to an even greater extent and a further labelled selective antibody is used instead of radiolabelled TSH, the above distinction between "primary competitor" and "secondary competitor" may become less unambiguous or even completely lose its meaning. This changes nothing concerning the assay principle of the receptor binding assay according to the invention and concerning the fact that such assays too are protected by the present invention.

By virtue of the fact that the method according to the invention permits immobilization of the TSH receptor complex formed in the measuring solution with a tracer bound directly to said complex or with a tracer introduced after the immobilization, and because furthermore reagents having tracers other than radionucleids can be used, the practical handling of TSH receptor autoantibody assays can be adapted very much better than was possible in the past to requirements of clinical practice. The incubation schemes, too, can be varied, and the incubation scheme described in the following Examples no longer appears essential.

Plastic surfaces, microparticles, magnetic particles, filters, polymer gel materials and other known solid-phase substrates can be used as solid phases. The possibility of using labelled autoantibodies and immobilized TSH (regarding the capability of TSH receptors for binding to immobilized TSH, cf. Leedman, P. J. et al., J. Clin. Endocrinol. Metab. 69, pages 134–141, 1989) will considerably increase the range of use of the assay, in particular with respect to a free choice of suitable direct or indirect tracers. By means of the method according to the invention, it is also possible to automate TSH receptor autoantibody assays. Thus, the assay design can be adapted in such a way that it can be carried out on known automatic systems (cf. for example Elecsys system from Boehringer Mannheim or ACS 180 system from Ciba Corning). In such automated systems, pipetting is carried out in the course of automatic handling of the samples, magnetic particles which are coated with a suitable specific antibody against the TSH receptor or with TSH, as a premix with labelled TSH or with a freely labelled antibody (e.g. ruthenium complex-labelled or acridinium ester-labelled) can then be admixed and finally basically any suitable TSH receptor material is added. After the incubation, conventional solid-liquid separation is possible, and the signal can then be determined, optionally after triggering a signal by adding suitable reagents. The pipetting sequence stated by way of example is variable.

The method according to the invention is explained in more detail below on the basis of a specific embodiment, with reference to two Figures.

Figure 2:
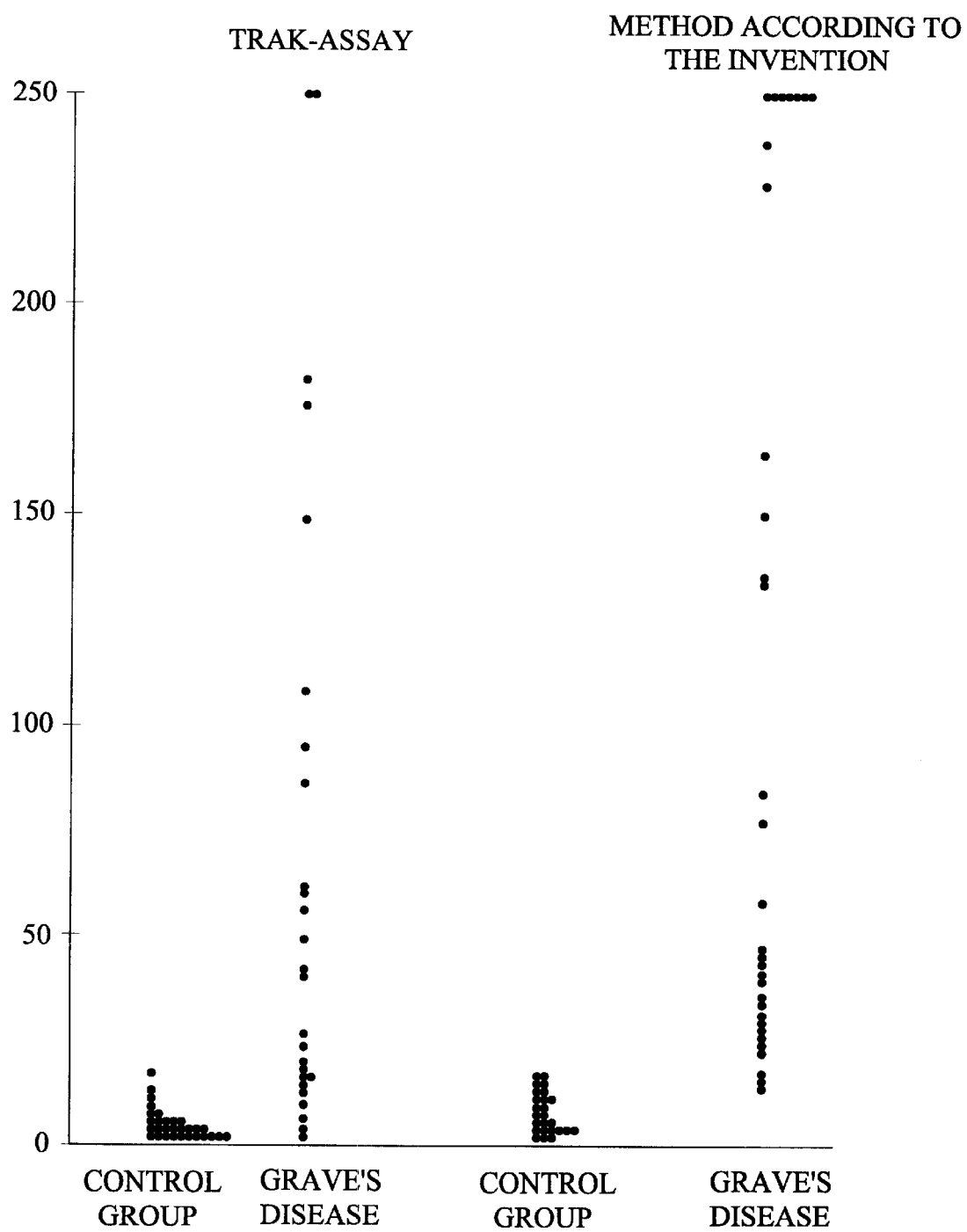

FIG. 1 shows a standard curve, obtained in the usual manner, for that embodiment of the method according to the invention which is described in the Example below and FIG. 2 shows a comparison of the measured results obtained by the method according to the invention and by the conventional radio receptor assay (TRAK-Assay® from B.R.A.H.M.S Diagnostica GmbH), in the case of the measurement of a group of patients suffering from Graves' disease.

DESCRIPTION OF EXPERIMENTS

Materials

In the experiments described below, various commercially available materials were used, in particular components of the TRAK-Assay® from B.R.A.H.M.S Diagnostica GmbH, an NAP25 desalination column from Pharmacia for purifying the antibody prepared for immobilization, Carbolink material from Pierce as solid-phase substrate material and sodium periodate from Fluka.

1. Preparation of Monoclonal Antibodies Against the TSH Receptor

Various monoclonal antibodies against selected peptides of the hTSH receptor were prepared by methods of the prior art (see above). A monoclonal antibody which is directed against a peptide and contains the amino acids 20 to 39 of the complete human TSH receptor (amino acid sequence GGMGCSSPBCECHQEEDFRV) was used for the further investigations.

2. Preparation of Monoclonal Antibodies Bound to the Solid Chase 250 mg of periodate are dissolved in 20 ml of an ascites solution which is diluted 1:10 with PBS (phosphate-buffered saline solution; 50 mM sodium phosphate, 100 mM NaCl, pH 7.5) and contains the above-mentioned monoclonal antibody, and incubation is carried out for 30 min at room temperature. The reaction solution is desalinated by the manufacturer's method over an NAP25 desalination column (Pharmacia). The desalinated protein is mixed with Carbolink material (10 ml) washed in PBS.

After incubation overnight with constant shaking at 4° C., 0.5 ml of the resulting gel with the monoclonal antibody bound thereon was filled into plastic columns (0.5×4 cm) and washed with 25 mM sodium citrate buffer, pH 2.5 (wash volume 2 ml). The columns were equilibrated in PBS (2 ml) and then used for further investigations.

3. With the Aid of the Columns Described, a Radio Receptor Assay was Carried Out Using Components of the TRAK-Assay® (B.R.A.H.M.S Diagnostica GmbH)

The radio receptor assay (preparation of the standard curves, measurement of patients' samples) was carried out according to the methods for carrying out the TRAK-Assay®. The following pipetting scheme was used:

50 µl of the sample are pipetted.

50 µl of solubilized porcine TSH receptor are then added by means of a pipette.

Incubation is carried out for 15 min at room temperature.

100 µl of tracer (TSH labelled with radioiodine) are added by means of a pipette.

The reaction batch obtained is transferred to the solid phase (column with Carbolink material) laden as above with the monoclonal antibody.

The reaction batch is incubated for one hour at room temperature.

The column is washed with 2 ml of PBS.

The radioactivity bound to the solid phase is measured in a gamma counter, this being done either with the direct use of the column containing solid phase or after elution of the bound proteins with 1 ml of 25 mM sodium citrate buffer, pH 2.5.

A corresponding procedure was used for preparing a standard curve for evaluating the results of the measurements of patients' sera, the standards from the commercial TRAK-Assay® being used, together with a standard which contains 2000 U TSH/ml.

Results

With the use of the standards, a standard curve (FIG. 1) was obtained which corresponded to that of a conventional TRAK-Assay®, i.e. increasing concentrations of added unlabelled TSH led to a decrease in the bound radioactivity.

On measuring serum samples of patients suffering from Graves' disease in the commercial TRAK-Assay® and by the method according to the invention, the following results were obtained:

Sera from 45 healthy control persons and from 39 patients suffering from Graves' disease were measured with the conventional TRAK-Assay® by the method according to the invention. The results of the measurements are summarized in Table 1.

The sera of patients suffering from Graves' disease originated from samples before the first therapy or within six weeks after the beginning of therapeutic measures.

TABLE 1

| No. | Control group (U/l) | | | | | Graves' disease (U/l) | | | |
|---|---|---|---|---|---|---|---|---|---|
| | TRAK-Assay | | Method acc. to the invention | | No. | TRAK-Assay | | Method acc. to the invention | |
| 1 | p | 12.3 | p | 16.4 | 1 | p | 42.3 | p | 31.3 |
| 2 | n | 1.2 | n | 6.4 | 2 | n | 3 | p | 27.7 |
| 3 | n | 7.2 | n | 13.7 | 3 | n | 6.1 | p | 44.2 |
| 4 | n | 3.8 | n | 7.9 | 4 | p | 15.5 | p | 41.5 |
| 5 | n | 7.2 | n | 4.7 | 5 | p | 936 | p | 966 |
| 6 | n | 1.7 | n | 6.5 | 6 | p | 15.5 | p | 47.4 |
| 7 | n | 3.4 | n | 9.7 | 7 | p | 108.3 | p | 164.8 |
| 8 | n | 4.4 | n | 1.1 | 8 | p | 16.4 | p | 26.7 |
| 9 | n | 3.8 | n | 1.2 | 9 | p | 26.3 | p | 84.7 |
| 10 | n | 2.5 | n | 12.4 | 10 | n | 9.4 | p | 58.9 |
| 11 | n | 4.7 | n | 7.8 | 11 | p | 56.3 | p | 239.2 |
| 12 | n | 2 | n | 2.3 | 12 | n | 3.4 | p | 17.3 |
| 13 | n | 10.6 | n | 1.3 | 13 | p | 19.5 | p | 34.1 |
| 14 | n | 1.1 | n | 1.4 | 14 | p | 13.2 | p | 229.1 |
| 15 | n | 3.9 | n | 1.5 | 15 | p | 40.3 | p | 29.8 |
| 16 | n | 2.1 | n | 1.6 | 16 | p | 15 | p | 25 |
| 17 | n | 2.5 | n | 1.7 | 17 | p | 23.6 | p | 271.7 |
| 18 | n | 3 | n | 1.8 | 18 | p | 18.6 | p | 46.6 |
| 19 | n | 4.8 | n | 1.9 | 19 | p | 697 | p | 671 |
| 20 | n | 1.8 | n | 2 | 20 | p | 60.8 | p | 150.6 |
| 21 | n | 3.1 | n | 2.1 | 21 | p | 86.5 | p | 133.7 |
| 22 | n | 9.3 | n | 2.2 | 22 | p | 19.3 | p | 27.3 |
| 23 | p | 16.6 | p | 15.5 | 23 | p | 26.8 | p | 47.5 |
| 24 | n | 2.1 | n | 2.3 | 24 | p | 61.4 | p | 255.9 |
| 25 | n | 4.9 | n | 10.2 | 25 | p | 49.3 | p | 135.6 |
| 26 | n | 4.9 | n | 2.5 | 26 | p | 149 | p | 439.5 |
| 27 | n | 5 | n | 12 | 27 | p | 16.7 | p | 28.6 |
| 28 | n | 1.8 | n | 2.6 | 28 | p | 176 | p | 303.2 |
| 29 | n | 2.9 | n | 2.7 | 29 | n | 1.1 | p | 14.9 |
| 30 | n | 2.6 | n | 2.8 | 30 | n | 1.2 | p | 17.1 |
| 31 | n | 7.9 | n | 2.8 | 31 | p | 182.3 | p | 644 |
| 32 | n | 4 | n | 2.9 | 32 | p | 23.7 | p | 40.5 |
| 33 | n | 2.5 | n | 13.6 | 33 | p | 17.8 | p | 23 |
| 34 | n | 1.9 | n | 2.9 | 34 | n | 1.3 | p | 15.6 |
| 35 | n | 1.8 | n | 10.1 | 35 | p | 95.1 | p | 77.8 |
| 36 | n | 2.3 | n | 5.2 | 36 | p | 19.8 | p | 36 |
| 37 | n | 1.9 | n | 1 | 37 | p | 13.7 | p | 165 |
| 38 | n | 2.3 | n | 1.1 | 38 | p | 12.8 | p | 29.9 |
| 39 | n | 5.7 | n | 2.9 | 39 | n | 9.8 | p | 14.7 |
| 40 | n | 6.4 | n | 1.2 | | | | | |
| 41 | n | 1.6 | n | 5.9 | | | | | |
| 42 | n | 1.6 | n | 1 | cut off | | 11.0 | | 14.0 |
| 43 | n | 1.5 | n | 1.9 | | | | | |
| 44 | n | 4 | n | 5 | | | | | |
| 45 | n | 1.4 | n | 5 | | | | | |
| Mv | | 4.09 | | 4.88 | | | | | |
| 1 s | | 3.18 | | 4.40 | | | | | | p = TSH receptor autoantibody positive
n = TSH receptor autoantibody negative

The mean value for the measurement of the autoantibody-free sera of the control group (n-45) is 4.1±6.4 (2s) U/ml for the TRAK-Assay® and 4.8±8.8 (2s) U/ml in the method according to the invention.

To maintain a comparable specificity of 95.5% in both tests, the cut-off (boundary between values for negative and positive samples) were specified at 11 U/ml for the conventional method and at 14 U/ml for the method according to the invention. Using these cut-off values, 79.5% of the patients suffering from Graves' disease (31 out of 39) were rated as positive in the established TRAK-Assay® radio receptor method.

A measurement of the same group of patients by the method according to the invention surprisingly showed that 100% of the patients suffering from Graves' disease (39 out of 39) were measured autoantibody-positive. The samples determined as negative in the conventional TRAK-Assay® (samples No. 2, 3, 12, 29, 30, 34, 39) were clearly rated as positive by the method according to the invention.

Moreover, a further advantage of the method according to the invention was that the predominant part of the samples was found to have a significantly stronger measured signal. The results obtained are shown graphically by way of illustration in FIG. 2.

Owing to the additional possibility, existing in the method according to the invention, of disturbing the interaction between a specific antibody bound to a solid phase and the TSH receptor complex with radiolabelled TSH bound thereto by autoantibodies present in the sample, not only is the clinical value of the assay for diagnosing Graves' disease, increased but also a substantially stronger and hence more reliable measured signal is generated by the method according to the invention in the case of patients identified as positive in both tests. The clinical value of the determination of TSH receptor autoantibodies, the occurrence of which is characteristic of Graves' disease, is thus decisively increased.

What is claimed is:

1. Competitive receptor binding assay for the determination of TSH (thyroid-stimulating hormone) receptor autoantibodies in a biological sample, comprising reacting the sample, in a liquid reaction mixture, with
   (i) a labeled solubilized TSH receptor preparation,
   (ii) a labeled primary competitor for at least a first portion of the TSH receptor autoantibodies in the sample, and
   (iii) an agent for immobilizing complexes formed between said TSH receptor and components of the reaction mixture,
   and detecting the amount of the primary competitor immobilized in the TSH receptor complexes,
   wherein the presence and/or amount of the TSH receptor autoantibodies are determined on the basis of the amount of the primary competitor immobilized in the TSH receptor complexes, and
   wherein the agent for immobilizing the complexes is at least one specific monoclonal or polyclonal antibody bound to a solid phase that specifically recognizes a defined partial peptide sequence on the TSH receptor selected from the group consisting of amino acids 20–39, (SEQ ID NO:1) 32–54, (SEQ ID NO:2) 287–301 SEQ ID NO:3, 361–381, SEQ ID NO:4 and 739–758 SEQ ID NO:5 of the amino acid sequence of the complete TSH receptor including the signal peptide without impairing the binding capability of the TSH receptor with respect to the TSH receptor autoantibodies or with respect to the primary competitor.

2. Receptor binding assay according to claim 1, wherein the agent for immobilizing complexes acts as a secondary competitor for at least a second portion of the TSH receptor autoantibodies in the sample, which competes for an epitope of the TSH receptor not recognized by the primary competitor and which does not compete with the binding of the primary competitor to the TSH receptor.

3. Receptor binding assay according to claim 1, wherein said primary competitor TSH receptor antibody competes with autoantibodies from the sample for the same or similar epitopes of the TSH receptor as labeled TSH.

4. Receptor binding assay according to claim 2, wherein said specific antibody bound to the solid phase competes as a secondary competitor with such TSH receptor autoantibodies from the sample whose occurrence is indicative for Graves' disease, but which do not compete with TSH.

5. Receptor binding assay according to claim 2, wherein said specific antibody is used in labeled form as a secondary competitor present in the liquid state, and wherein TSH bound to the solid phase is used as the primary competitor and as the agent for immobilizing the formed TSH receptor complex.

6. Receptor binding assay according to claim 5, wherein said TSH receptor autoantibodies competing with the secondary competitor belong to the class of thyroid stimulating autoantbodies.

7. Receptor binding assay according to claim 1, wherein said specific antibody was obtained by immunization of a mouse with a recombinant partial TSH receptor comprising the extracellular domain or an extracellular loop of the membrane anchored domain of a TSH receptor, and by fractionating the resulting antibodies by affinity chromatography on a stationary phase carrying the same partial peptides of the partial TSH receptor as used for the immunization.

8. Receptor binding assay according to claim 1, wherein said specific antibody is a monoclonal antibody prepared by immunization of a mouse with a recombinant partial TSH receptor comprising the recombinant extracellular part of a TSH receptor of a shorter partial peptide thereof, subsequent fusion of antibody-producing mouse splenocytes with myelocytes, selection of individual antibody-producing hybridoma cells, and cultivation thereof.

9. Receptor binding assay according to claim 1, wherein as solid phase a substrate selected from the group consisting of particles, test tubes or microtiter plates made of plastic or glass, magnetic polymer particles, polymer gels and filters is used, and wherein said agent for immobilizing the formed TSH receptor complexes from the liquid reaction mixture is bound directly or indirectly to such substrate.

10. Receptor binding assay according to claim 2, wherein a tracer selected from the group consisting of a radionuclide, an enzyme, an enzyme substrate, and a component of a chemiluminescent or fluorescent labeling system is used for labeling the primary or secondary competitor.

11. Receptor binding assay according to claim 2, wherein one of the primary or secondary competitors is bound to a first component of a specific binding pair and the TSH receptor complexes formed are labeled or immobilized by reaction with a reactant comprising the second component of the specific binding pair, which second component is either bound to a detectable tracer or to a solid phase.

12. Receptor binding assay according to claim 1, wherein said TSH receptor autoantibodies to be determined are thyroid stimulating autoantibodies, the occurrence of which in human serum is indicative of Graves' disease.

13. Reagent kit for carrying out a competitive receptor binding assay according to claim 1 containing
 (i) a solubilized TSH receptor preparation,
 (ii) a primary competitor selected from the group consisting of labeled TSH and a labeled specific TSH antibody, and
 (iii) a solid-phase substrate to which an agent for separating formed TSH receptor complexes from the liquid reaction mixture is bound, which agent is selected from the group consisting of a specific TSH receptor antibody and TSH.

14. Competitive receptor binding assay for the determination of TSH (thyroid-stimulating hormone) receptor autoantiodies in a biological sample, comprising reacting the sample, in a liquid reaction mixture, with
 (i) a solubilized TSH receptor preparation,
 (ii) a known amount of a labeled TSH as primary competitor for at least a first portion of the TSH receptor autoantibodies in the sample, and
 (iii) an agent for immobilizing TSH receptor complexes formed in the reaction mixture, wherein the presence and/or amount of the TSH receptor autoantibodies are determined on the basis of the amount of the labeled TSH in the immobilized TSH receptor complexes,
 and detecting the amount of the labeled TSH immobilized in the TSH receptor complexes,
 wherein the presence and/or amount of the TSH receptor autoantibodies are determined on the basis of the amount of the labeled TSH immobilized in the TSH receptor complexes, and
 wherein the agent for immobilizing the complexes is at least one specific monoclonal or polyclonal antibody bound to a solid phase that specifically recognizes a partial peptide sequence of the TSH receptor selected from the group consisting of amino acids 20–39 SEQ ID NO:1, 32–54, SEQ ID NO:2 287–301 SEQ ID NO:3, 361–381 SEQ ID NO:4, and 739–758 SEQ ID NO:5 of the amino acid sequence of the complete TSH receptor including the signal peptide without impairing the binding capability of the TSH receptor with respect to the TSH receptor autoantibodies or with respect to the labeled TSH.

15. Receptor binding assay according to claim 14, wherein the agent for immobilizing complexes simultaneously acts as a secondary competitor for at least a second portion of the TSH receptor autoantibodies, which competes for an epitope of the TSH receptor not recognized by the labeled TSH and which does not compete with the binding of the labeled TSH to the TSH receptor.

16. Receptor binding assay according to claim 14, wherein said selective antibody bound to the solid phase competes as a secondary competitor with such TSH receptor autoantibodies from the sample whose occurrence is indicative of Graves' disease but which do not compete with TSH.

17. Receptor binding assay according to claim 16, wherein said TSH receptor autoantibodies competing with the secondary competitor belong to the class of thyroid stimulating autoantibodies.

18. Receptor binding assay according to claim 14, wherein said specific antibody was obtained by immunization of a mouse with a recombinant partial TSH receptor comprising the extracellular domain or an extracellular loop of the membrane-anchored domain of a TSH receptor, and by fractionation of the resulting antibodies by affinity chromatography on a stationary phase carrying the same partial peptides of the partial TSH receptor as used for the immunization.

19. Receptor binding assay according to claim 14, wherein said specific antibody is a monoclonal antibody prepared by immunization of a mouse with a recombinant partial TSH receptor comprising the recombinant extracellular part of a TSH receptor or a shorter partial peptide thereof, fusion of antibody-producing mouse splenocytes with myelocytes, selection of individual antibody-producing hybridoma cells, and cultivation thereof.

* * * * *